(12) United States Patent
Gilchrist et al.

(10) Patent No.: US 6,187,290 B1
(45) Date of Patent: *Feb. 13, 2001

(54) PHYSIOLOGICALLY ACCEPTABLE FOAMABLE FORMULATION AND FOAM

(75) Inventors: Thomas Gilchrist, Ayr; Eilidh Gilchrist, Prestwick, both of (GB)

(73) Assignee: Giltech Limited, Ayr (GB)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 08/836,246

(22) PCT Filed: Dec. 5, 1995

(86) PCT No.: PCT/GB95/02830

§ 371 Date: May 7, 1997

§ 102(e) Date: May 7, 1997

(87) PCT Pub. No.: WO96/17595

PCT Pub. Date: Jun. 13, 1996

(30) Foreign Application Priority Data

Dec. 6, 1994 (GB) .................................................. 9424562

(51) Int. Cl.⁷ .............................. A61K 9/12; A61K 33/00
(52) U.S. Cl. ............................. 424/45; 424/46; 424/443; 424/78.02; 424/618; 424/630; 424/641; 424/614; 424/649; 424/613; 424/78.07; 424/620; 424/657; 424/667; 424/655; 424/639; 514/944; 514/945; 514/938

(58) Field of Search .......................... 510/370; 523/218; 424/45, 46, 443, 78.02, 618, 630, 641, 614, 649, 78.07; 514/945, 944, 938

(56) References Cited

U.S. PATENT DOCUMENTS

| | | |
|---|---|---|
| 4,086,331 | 4/1978 | Neumann . |
| 4,948,575 * | 8/1990 | Cole et al. . |
| 5,089,606 * | 2/1992 | Cole et al. . |
| 5,718,916 * | 2/1998 | Scherr . |
| 5,851,461 * | 12/1998 | Bakis et al. . |

FOREIGN PATENT DOCUMENTS

| | | |
|---|---|---|
| 0 380 254 A2 | 8/1990 | (EP) . |
| 586260 | 3/1994 | (EP) . |
| 1 503 897 | 3/1978 | (GB) . |
| 2207865 | 2/1989 | (GB) . |
| 4282311 | 10/1992 | (JP) . |
| 94/00512 | 1/1994 | (WO) . |

* cited by examiner

*Primary Examiner*—Raj Bawa
(74) *Attorney, Agent, or Firm*—Ratner & Prestia

(57) ABSTRACT

There is described a foamable formulation comprising a foamable carrier and an active ingredient which may be admixed with the carrier or packaged separately and dispersed into the carrier during the foaming process. Alginate gel is a preferred foamable carrier. The foam produced from such a formulation, and a foam sheet produced by drying the foam, also form part of the invention. The formulation, foam and foam sheet are especially useful for medical applications, for example in treating burns. As apparatus to store the components of the formulation and to generate the foam is also described.

13 Claims, No Drawings

PHYSIOLOGICALLY ACCEPTABLE FOAMABLE FORMULATION AND FOAM

The present invention is concerned with a foamable formulation and the foam formed therefrom.

BACKGROUND OF THE INVENTION

A wide variety of gels, creams, ointments, lotions etc are available for application to a body surface. The exact content of such compositions generally depends upon the purpose of application which may be, for example, to clean a body surface, to promote healing of any wound or injury, to prevent an exposed area of the body from drying out, to prevent infection etc. In certain circumstances the composition may include an active ingredient which is administered to the patient by application of the composition.

One example of a commercially available gel in INTRA-SITE™ produced by Smith & Nephew Ltd. This hydrogel contains hydrated carboxymethylcellulose as its main ingredient, and is applied to wounds in gel form as a primary treatment in order to clean the exposed surface by aiding removal of cell debris, dirt etc. In addition to acting as a sloughing agent, the gel also keeps the wound from drying out, thereby promoting healing.

Another example of a gel suitable for use on a wound dressing is described in EP-A-0586260 of Courtaulds Fibres Ltd. The gel disclosed is an alginate gel having an alginate content of 2 to 11 percent by weight.

SUMMARY

Viewed from one aspect, the present invention provides a formulation for application to a body surface as a foam, said formulation comprising an active ingredient and a foamable, preferably physiologically acceptable, carrier. The active ingredient(s) may be present as an integral part of the formulation, or may be held separately to other ingredients of the formulation, being combined therewith during formation of the foam. Optionally, the formulation may also comprise a foaming agent (for example a surfactant) which is capable of promoting production of a foam structure.

DETAILED DESCRIPTION OF THE PREFERRED EMBODIMENTS

In one embodiment, the present invention provides a, physiologically acceptable (preferably pharmaceutically acceptable), foamable carrier and an active ingredient packaged separately thereto which is admixed with the foamable carrier during the foaming process.

The term "active ingredient" is used herein to refer to any agent which affects the metabolism or any metabolic or cellular process of the patient (including growth factors nutrients and living cells), promotes cleaning of the area to which it is applied (for example aids removal of a debris, dirt, bacteria, malodours and the like), combats infection, hypergranulation, inflanmation and/or aids healing.

The term "foamable carrier" refers to any ingredient which is compatible with the active ingredient and which is capable of forming a foam. Conveniently the foamable carrier does not affect the function of the active ingredient in a detrimental manner. Desirably the foamable carrier is non-irritant when maintained in contact with a body surface for several hours. The foamable carrier may be a gel, for example an alginate gel.

The foam produced may be maintained on the body area, to form a protective covering, for example over a wound. Additionally, the foam may deliver the active ingredient, preferably in a controlled release manner. In one embodiment the foam acts as a transdermal delivery system. The foam may be exposed to the atmosphere so that it dries into a coating, or may be covered by conventional dressings.

As an example, the foam may be used to treat dermatological conditions (including psoriasis, atopic and allergic eczema). It may be convenient in this embodiment for the foam to deliver an active ingredient normally used to alleviate such conditions, for example a steroid such as hydrocortisone.

In another embodiment the foam may be used to treat burns or scalds, including sunburn.

In another embodiment the foam may be applied cosmetically, and for example may include skin moisturising agents, nutrional agents and growth factors suitable to promote skin regeneration. A foam intended for cosmetic use may include colorants or pigments so that the foam may be applied to the skin as a cosmetic or to disguise any blemishes in the skin.

The foam may be used prophylactically. In particular a foam containing a UV blocking agent may be applied to exposed areas of the skin to protect it from the effects of the sun.

The formulation of the invention is applied to the body site of interest in the form of a foam and it is therefore essential that the composition undergoes a foaming process before application to the body. In the foaming process gas is forced into or is formed within the formulation to entrap small bubbles of gas therein, thereby forming the foam. Any suitably gas or gas producing system can be used to produce the foam. Mention may be made of butane and nitrous oxide, but other gases are also suitable. Conveniently the foam may be produced by conventional means such as by using aerosol technology.

The formulation according to the present invention may be stored in any convenient container until required. Generally, the container will be designed to preserve the sterile nature of the formulation. Conveniently the container will be provided with means to foam the composition when required.

Thus the present invention also provides an apparatus which produces a physiologically acceptable foam as described above. Generally, the foam will be produced from sterile ingredients.

Viewed from another aspect, the present invention provides a closed container, containing therein a formulation as described above, said container being capable of expelling said formulation in the form of a foam. For example, the container may be an aerosol canister, containing a pressurized gas which in use causes production of the foam. Alternatively, the gas may be produced by a chemical reaction when two different ingredients (for example contained in two portions of a sachet) are admixed together. In one embodiment the closed container has separate reservoirs for the foamable carrier and the active ingredient. Thus, the foamable carrier and the active ingredient are stored separately during storage and are admixed together in suitable proportions during the foaming process.

The present invention thus provides an apparatus to produce a foam for application to a body surface, from a formulation as defined above, said apparatus comprising:

a. a closed container having
  i) a reservoir containing said foamable carrier;
  ii) a reservoir containing said active ingredient; and b. foaming means to produce a foam from said foamable carrier.

Optionally a foaming agent may be mixed with the foamable carrier.

Prior to the foaming process, the foamable carrier is preferably in the form of a gel. The gel may be sterilised and this is generally desirable where the foam is intended for medical use. Usually, sterilisation will take place by autoclaving the formulation, since this is currently the most economic means of achieving sterilisation. Autoclaving at temperatures of from 100° C. to 125° C. for under ½ hour is normally sufficient. Generally, the autoclaving process should be as mild as possible, whilst being sufficient to sterilise the formulation. For example, autoclaving at temperatures of about 121° C. for 15–20 minutes is acceptable. The autoclaved formulation may then be foamed when cool. It is also possible, however, to sterilise the formulation by other means, for example by γ-irradiation or e-beam irradiation. It has been found that autoclaving the gel may cause the MW of the foamable carrier to be slightly reduced. Consequently it may be desirable to select a foamable carrier having a higher MW than that ultimately required.

The foam forms an air-tight cover around any wound or injury to which it is applied, and this prevents that area from drying out and may also combat infection. The advantages of applying a topical product in the form of a foam include:

1. Easy rapid application,
2. Conforms to surface irregularities,
3. Insulates the wound,
4. Cools the tissues,
5. Offers antibacterial action to prevent infection,
6. Biocompatibility with tissue,
7. Suitable for use as a vehicle for the administration of pharmaceutical agents, and/or
8. Maintains a moist environment.

It has been observed that the foam produced from the formulation of the present invention may subside over a period of time (for example 3 to 24 hours, especially 6 to 12 hours) as some of the gas entrapped in the foam structure escapes. The foamed formulation gradually dries to produce a foam (i.e. closed cell) sheet which still retains a basic foam structure and which may cover the site to which the foam was applied. This foam sheet can be left in place as a protective cover over a wound, may be used to deliver an active ingredient to the site, etc. It is possible to produce the sheet separately as a dressing for a wound or injury for direct application in that form. The foam sheet is therefore a yet further aspect of the present invention.

Generally, the formulation of the present invention will be applied directly to the body site of interest in the form of a foam, the foam being produced from any suitable device (such as an aerosol) immediately before application. It is, however, possible for a quantity of the foamed formulation to be produced and then applied onto the body site by any suitable means, for example by hand or by spatula. This method may be required for wounds having a narrow opening.

As stated above, the foam may also be produced on a suitable surface and then dried to produce the foam sheet described above. Generally, the production of the sheet will take place under sterile conditions. The sheet may be divided into a convenient size and may be packaged. Optionally the foam sheet may be produced on contoured surface so that it is moulded to a pre-determined shape.

It has further been observed that where the foam is covered with an airtight cover (for example a plastics backing) the foam structure is maintained, without collapsing to a foam sheet. Covering the freshly produced foam with a plastics cover (for example a plastics film or a plastics bag) may be desirable in circumstances where the bulk of the foam is to be retained.

Examples of suitable foamable carriers for use in the composition of the present invention include (but are not limited to) alginate and derivatives thereof, carboxymethylcellulose and derivatives thereof, collagen, polysaccharides (including, for example, dextran, dextran derivatives, pectin, starch, modified starches such as starches having additional carboxyl and/or carboxamide groups and/or having hydrophillic side-chains, cellulose and derivatives thereof), agar and derivatives thereof (such as agar stabilised with polyacrylamide), polyethylene oxides, glycol methacrylates, gelatin, gums such as xanthum, guar, karaya, gellan, arabic, tragacanth and locust bean gum. Also suitable are the salts of the aforementioned carriers, for example, sodium alginate. Mixtures of any of the aforementioned carriers may also be used, as required.

Preferred foamable carriers include alginate, carboxymethylcellulose, the derivatives and salts thereof and mixtures of any of these. Alginate (the derivatives or salts thereof, such as sodium and calcium alginate) are especially preferred. Foamable carriers having a molecular weight of from 10,000 to 200,000 kDa are preferred, especially over 100,000 kDa, for example 150,000 to 200,000 kDa, may be used.

The formulation may further comprise a foaming agent, which promotes the formation of the foam. Any agent having a surfactant character may be used. The surfactants may be cationic, non-ionic or anionic. Examples of suitable foaming agents include cetrimide, lecithin, soaps, silicones and the like. Commercially available surfactants such as Tween™ are also suitable. Cetrimide (which additionally has an anti-bacterial activity) is especially preferred.

The formulation of the present invention (and thus the foam) may be used to deliver pharmaceutically active agents, in particular to deliver such agents in a controlled release manner. Mention may be made of:

Antisepitics, Antibacterials and Antifungal agents, such as Chlorhexidine, acetic acid, polynoxylin, povidone iodine, mercurochrome phenoxyethanol, acridene, silver nitrate, dyes eg brilliant green, undecanoic acid, silver sulphadiazine, silver proteins and other silver compounds, metronidazole, benzaclonium chloride;

Nutritional agents, such as vitamins and proteins;

Growth factors and healing agents, including Ketanserin a serotonomic blocking agent;

Living Cells;

Enzymes include streptokinase and streptodormase;

Elements—zinc, selenium, cerium, copper, manganese, cobalt, boron, arsenic, chromium silver, gold, gallium;

Charcoal;

Desloughing and Debriding agents such as hypochlorite and hydrogen peroxide;

Astringents including potassium permanganate;

Antibiotics exemplified by neomycin and framycetin sulphate, sulfamylon, fusidic acid, mupirocin, bacitracin, gramicidin.

A particularly convenient way of presenting metal ions (for example silver or calcium ions) is via a glass composition. The glass may be ground into particle form and then incorporated into the formulation of the present invention. Optionally the glass is capable of sustained or delayed release of the metal ions. Reference may be made to WO-A-90/08470 of Giltech Ltd which describes a suitable glass composition for delivering silver ions. Thus, a preferred embodiment of the invention is a formulation as described above wherein particles of a metal ion (preferably silver and/or calcium ion) releasing glass are admixed into the formulation during the foaming process.

Other preferred pharmaceutically active agents include Chlorhexidine, povidone iodine and cetrimide.

In addition the formulation of the present invention may further comprise other conventional additives such as plasticisers and humectants (such as glycerol, propane-1,2-diol, polypropylene glycol and other polyhydric alcohols), free radical scavengers to stabilise against the effects of sterilisation by irradiation, viscosity-adjusting agents, dyes and colorants, and the like.

Particularly preferred formulations of the present invention include:

1. Alginate/cetrimide
    alone or with chlorohexidine or povidone iodine or other agents.
Uses
    a. Hand and body washing (including scalp shampoo);
    b. Topic agents for skin carriage sites and wounds.
2. Alginate/cetrimide/calcium and silver ion releasing glass (eg Arglaes™)
    alone or with other agents
    The calcium released from the glass will stabilise the alginate by forming the insoluble calcium salt.
Uses
    a. Silver is effective against gram negative species eg Proteus, *E Coli,* Pseudomonas & Klebsiella aerobacters;
    b. Cetrimide is a broad spectrum antibacterial and antifungal agent, most effective against gram positive species eg *Staphylococcus epiderimis* and *aureus* (wounds are generally infected on a 50:50 basis with gram positive or negative species); and
    c. sloughy wounds, granulating or epithilialising wounds, black necrotic tissue, clinically infected wounds, malodorous wounds and burns and scalds and as a haemostat.
3. Hydrogel foams in general
    eg Carboxymethylcellulose
    eg Gelatin—preformed foam could provide an improved presentation for burn coverings, temporary soft tissue implants, etc.
4. Mixtures
    eg Alginate/collagen mixtures.

Alginates are particularly preferred as the foamable carrier in the formulation of the present invention. Alginates are especially useful for application to wounds since the alginate promotes the healing process and is itself slowly absorbed and metabolised in the body. Sodium alginate is soluble whereas calcium alginate is insoluble. In the present invention therefore it is desirable for a careful mixture of sodium and calcium alginate to be produced, the exact ratio being altered in accordance with the desired characteristics of the foam. An alginate-based foam may therefore be easily removed simply by washing away in saline. Commercially available alginates suitable for use in the present invention include Manucol DMF, Manucol LKX, and Keltone™ for example Keltone HV™ which is a finely ground fibrous sodium alginate suitable for use in food preparations. High molecular weight alginates are preferred, for example these having a molecular weight of 50,000 kDa or above, for example 100,000 to 200,000 kDa.

The present invention further provides the use of a formulation for production of a foam suitable for medical or veterinary purposes, especially for the controlled released delivery of the active ingredient.

For example, the present invention provides the use of a formulation to produce a foam suitable for application to wounds or injuries, especially burns. The invention further provides the use of a formulation to produce a foam which delivers an active ingredient, such as a cleaning agent or a medicament to the body. For example, the foam produced may be used as a soap alternative for doctors or other medical staff to clean their hands before seeing a patient. Use of the foam could eliminate the need for washing in water.

Additionally, the present invention provides the use of the foam itself for application (in particular topical application) to a body. Therefore the foam may be used to deliver a drug or any other medicament, may be used as a sloughing agent to clean a wound etc, or may be used to provide a sterile covering for a wound etc.

The present invention also provides the use, separately, of the container, of the composition and of the foam described above to produce a wound dressing in the form of a foam sheet.

In a further aspect, the present invention provides a method of treatment of the human or animal (preferably mammalian) body, said method comprising administering to said body a foam or a foam sheet as hereinbefore defined. Optionally the foam and/or foam sheet may deliver a drug or a medicament to the body.

The foam and the foam sheet of the present invention are especially suitable for treatment of burns.

The present invention will now be described with reference to the following examples:

Unless otherwise stated, the percentage amounts of ingredients are given on a percentage by weight basis.

EXAMPLE 1

A composition according to the present invention was formed by admixing the following ingredients together:

3% Manucol LKX
1% Cetrimide
80:20 di-ionised water:propan-1,2-diol
3% Arglaes (a silver ion releasing glass)

A gel composition was formed and autoclaved at approximately 121° C. for 15 to 20 minutes. The gel produced was firm but mobile.

The gel was foamed using an aerosol canister and a fine celled, highly conformable, thick, creamy foam was produced. There was little slump, little flow, fairly stable, did not go back to a gel when rubbed. The foam was cool and soothing. Once left to dry the flat foam left is still moist, cool sponge. The silver presence was showing.

EXAMPLE 2

A composition according to the present invention was formed by admixing the following ingredients together:

3% Manucol DMF
1% Cetrimide
80:20 di-ionised water:propan-1,2-diol

A gel composition was formed and autoclaved at approximately 121° C. for 15 to 20 minutes. The gel produced was firm but mobile.

The gel was foamed using an aerosol canister and a fine celled, highly conformable, thick foam was produced. There was no slump or flow. The foam was very stable and did not go back to a gel when rubbed. It was cool and soothing. Once left to dry the flat foam left was still moist, fragile and sponge-like.

EXAMPLE 3

A composition according to the present invention was formed by admixing the following ingredients together:

3% Keltone
1% Cetrimide
80:20 di-ionised water:glycerol

A gel composition was formed and autoclaved at approximately 121° C. for 15 to 20 minutes. The gel produced was firm but mobile.

The gel was foamed using an aerosol canister and a fine celled, thick foam was produced. There was no slump or flow. The foam was very stable, had a dry feeling, plasticity, and did not go back to a gel when rubbed. It was cool and soothing. Once left to dry the flat foam was still moist, fragile and sponge-like.

EXAMPLE 4

A composition according to the present invention was formed by admixing the following ingredients together:

350 mls di-ionised water
2 gms Cetrimide
20 gms Carboxymethylcellulose
40 mls Glycerin A gel composition was formed. The gel produced was very sticky.

The gel was foamed using an aerosol canister and a thixotropic, minimum flow, fine cellular foam was formed. It had a thick texture that was virtually unchanged when left overnight.

EXAMPLE 5

A composition according to the present invention was formed by admixing the following ingredients together:

80 mls di-ionised water
2 gms Cetrimide
20 mls Glycerin
4 gms Carrageenan

A gel composition was formed. The gel produced was thick and foamed slightly when cetrimide was added (acts like an alginate).

The gel was foamed using an aerosol canister and a thixotropic, minimum flow, fine cellular foam was formed. It did not collapse to touch and was difficult to break down into a gel again. After being left overnight it was sticky and non-cohesive.

EXAMPLE 6

A composition according to the present invention was formed by admixing the following ingredients together:

60 mls di-ionised water
1.2 gms Cetrimide
4 mls Gelatin

A gel composition was formed. The gel produced was firm and rigid. Just before foaming 60 mls boiling di-ionised water was added and a warm liquid was formed. When pressurised the temperature dropped.

After the liquid reached the correct temperature within the foaming canister a thick fully expanding foam was produced. It was fine celled and did not break down easily. Initially it was non-thixotropic and then developed into a stable foam. Overnight a firm closed cell sponge with very good handling strength was produced.

EXAMPLE 7

A composition according to the present invention was formed by admixing the following ingredients together:

80 mls di-ionised water
1 ml Tween 80
3 gms Keltone
20 mls glycerin

A gel composition was formed. The gel produced was firm but mobile.

The gel was foamed using an aerosol canister and a fine celled, thick, thixotropic foam was produced that stabilised very quickly.

EXAMPLE 8

A composition according to the present invention was formed by admixing the following ingredients together:

3% Keltone
1% Cetrimide
80:20 di-ionised water:glycerol
4% povidone iodine

A gel composition was formed and autoclaved at approximately 121° C. for 15 to 20 minutes. The gel produced was firm but mobile.

The gel was foamed using an aerosol canister and a fine celled, thin foam was produced that stabilised overnight into a sponge with good handling strength.

EXAMPLE 9

A composition according to the present invention was formed by admixing the following ingredients together:

3% Keltone
1% Cetrimide
80:20 di-ionised water:glycerol

A gel composition was formed and autoclaved at approximately 121° C. for 15 to 20 minutes. The gel produced was firm but mobile.

Just before foaming 6 g Arglaes powder (ie powdered metal ion releasing glass) was added and the gel was immediately foamed using an aerosol canister. A fine celled, white foam was produced that eventually stabilised into a firm sponge pad.

EXAMPLE 10

A composition according to the present invention was formed by admixing the following ingredients together:

3% Keltone
1% Cetrimide
80:20 di-ionised water:glycerol
0.1 g Chlorohexidine

A gel composition was formed and autoclaved at approximately 121° C. for 15 to 20 minutes. The gel produced was firm but mobile.

The gel was foamed using an aerosol canister and a fine celled, thick foam was produced that stabilised overnight into a sponge pad.

EXAMPLE 11

A composition according to the present invention was formed by admixing the following ingredients together:

2½% Keltone

2½% Carboxymethylcellulose

1% Cetrimide

80:20 di-water:glycerol

The gel composition formed was autoclaved at approximately 121° C. for 15 to 20 minutes. The gel produced was firm but mobile.

The gel was foamed using an aerosol canister and a fine celled, highly conformable, foam was produced. There was little slump or flow, the foam was fairly stable, cool and soothing. Once left to dry the flat foam sheet was a still moist, cool sponge.

EXAMPLE 12

A composition according to the present invention was formed by admixing the following ingredients together:

2% Keltone

2% Hydroxypropylcellulose

1% Cetrimide

80:20 di-water:glycerol

The gel composition formed was autoclaved at approximately 121° C. for 15 to 20 minutes. The gel produced was thick but mobile.

The gel was foamed using an aerosol canister and a fine celled foam was produced. There was little slump or flow, the foam was fairly stable, cool and soothing. Once left to dry the flat foam sheet was a still moist, cool sponge.

What is claimed is:

1. A physiologically acceptable foam for application to a body, said foam comprising a physiologically acceptable foamable carrier selected from the group consisting of alginate, carboxymethylcellulose, collagen, polysaccliarides, agar, polyethylene oxides, glycol methacrylates, gelatin, xanthum, guar, karaya, gellan, arabic, tragacanth and locust bean gums, the salts thereof, and mixtures thereof, and an active ingredient in particulate form dispersed in said foam, said active ingredient being packaged separately from said foamable carrier prior to foaming and is admixed with said foamable carrier only during the foaming thereof; said active ingredient being selected from the group consisting of chlorhexidine, acetic acid, polynoxylin, povidone iodine, mercurochrome phenoxyethanol, acridene, silver nitrate, silver sulphadiazine, dyes, undecanoic acid, silver compounds, metronidazole, benzaclonium chloride, vitamins, ketanserin, streptokinase, streptodormase, zinc, serium, copper, manganese, cobalt, chromium, silver, gold, boron, selenium, arsenic, gallium, charcoal, hypochlorite ions, peroxide ions, potassium permanganate, neomycin sulphate, framyclitin sulphate, sulfamylon, fusidic acid, mupirocin, bacitracin, gramicidin, water soluble glass containing at least one kind of metallic ion or boron; their salts, and mixtures thereof.

2. A formulation as claimed in claim 1, wherein said foamable carrier is selected from the group consisting of alginate, carboxymethylcellulose, salts thereof, and mixtures thereof.

3. A formulation as claimed in claim 1, wherein said foamable carrier has a weight average molecular weight of from 10,000 to 200,000 kDa.

4. A formulation as claimed in claim 1, wherein said active ingredient is selected from the group consisting of a silver ion releasing glass composition, chlorhexidine, povidone iodine and cetrimide.

5. A formulation as claimed in claim 1 further containing a foaming agent.

6. A formulation as claimed in claim 5, wherein said foaming agent is selected from the group consisting of cetrimide, lecithin, a soap, silicone and a surfactant.

7. A formulation as claimed in claim 1 in foamed form, wherein said active ingredient is evenly distributed throughout the foam.

8. A formulation as claimed in claim 1 in the form of a foam sheet.

9. A formulation as claimed in claim 1 wherein said foamable carrier provides controlled release of said active ingredient.

10. A formulation as claimed in claim 1 wherein said foamable carrier is sodium alginate and said active ingredient is a glass which releases both silver ions and calcium ions during dissolution.

11. A formulation as claimed in claim 1 wherein said foamable carrier is alginate.

12. A formulation as claimed in claim 1 wherein said foamable carrier is a foamable gel.

13. A formulation as claimed in claim 8 wherein said foam sheet is pre-formed and dried prior to application to a body.

* * * * *